(12) United States Patent
Hasenoehrl et al.

(10) Patent No.: US 7,115,551 B2
(45) Date of Patent: Oct. 3, 2006

(54) CLEANSING ARTICLES FOR SKIN OR HAIR

(75) Inventors: Erik John Hasenoehrl, Loveland, OH (US); James Michael Cosgrove, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 246 days.

(21) Appl. No.: 10/453,168

(22) Filed: Jun. 3, 2003

(65) Prior Publication Data

US 2003/0228351 A1 Dec. 11, 2003

Related U.S. Application Data

(60) Provisional application No. 60/387,305, filed on Jun. 7, 2002.

(51) Int. Cl.
*C11D 17/00* (2006.01)
*D04H 1/00* (2006.01)
*B32B 5/18* (2006.01)

(52) U.S. Cl. .................. 510/438; 15/208; 442/118; 442/123; 442/182; 442/198; 442/394; 442/414; 424/428; 428/402.2

(58) Field of Classification Search ............ None
See application file for complete search history.

(56) References Cited

U.S. PATENT DOCUMENTS

| | | | |
|---|---|---|---|
| 2,877,115 A | 3/1959 | Wemyss, Jr. et al. | |
| 2,944,931 A | 7/1960 | Yang | |
| 3,305,392 A | 2/1967 | Britt | |
| 3,424,643 A | 1/1969 | Lewis, Jr. et al. | |
| 3,451,758 A | 6/1969 | McClain | |
| 3,580,853 A | 5/1971 | Parran | |
| 3,632,396 A | 1/1972 | Perez-Zamora | |
| 3,686,025 A | 8/1972 | Morton | |
| 3,795,624 A | 3/1974 | Feinstone | |
| 3,895,128 A | 7/1975 | Gaiser | |
| 3,896,807 A | 7/1975 | Buchalter | |
| 3,939,260 A | 2/1976 | Lafon | |
| 3,944,694 A | 3/1976 | McQueary | |
| 3,949,137 A | 4/1976 | Akrongold et al. | |
| 3,956,551 A | 5/1976 | Richards | |
| 3,994,771 A | 11/1976 | Morgan, Jr. et al. | |
| 4,112,167 A | 9/1978 | Dake et al. | |
| 4,127,515 A | 11/1978 | McRae et al. | |
| 4,145,302 A | 3/1979 | Doan | |

(Continued)

FOREIGN PATENT DOCUMENTS

CN 1050066 A 3/1991

(Continued)

OTHER PUBLICATIONS

Vaughan, C.D., "Solubility Effects in Product Package, Penetration, and Preservation", Cosmetics & Toiletries, vol. 103, pp. 47-69 (Oct. 1968).

(Continued)

*Primary Examiner*—Necholus Ogden
(74) *Attorney, Agent, or Firm*—Jason J. Camp; Eileen L. Hughett (57) ABSTRACT

The present invention relates to disposable, personal cleansing articles useful for cleansing the skin or hair. These articles are used by the consumer by wetting the dry article with water and then rubbing the article against the skin or hair. The article comprises a water insoluble substrate with an elastomeric component and having a cleansing surface and a lathering surfactant releasably associated with the substrate. Preferably, the articles of the present invention further comprise a conditioning component.

14 Claims, 1 Drawing Sheet

U.S. PATENT DOCUMENTS

| | | | |
|---|---|---|---|
| 4,206,195 A | 6/1980 | Bolich, Jr. et al. |
| 4,206,196 A | 6/1980 | Davis |
| 4,271,272 A | 6/1981 | Strickman et al. |
| 4,303,543 A | 12/1981 | Mansy |
| 4,343,403 A | 8/1982 | Daniels et al. |
| 4,397,754 A | 8/1983 | Collishaw et al. |
| 4,462,981 A | 7/1984 | Smith |
| 4,515,703 A | 5/1985 | Haq |
| 4,525,411 A | 6/1985 | Schmidt |
| 4,553,275 A | 11/1985 | Goldstein |
| 4,559,157 A | 12/1985 | Smith et al. |
| 4,574,052 A | 3/1986 | Gupte et al. |
| 4,603,069 A | 7/1986 | Haq et al. |
| 4,683,001 A | 7/1987 | Floyd et al. |
| 4,690,821 A | 9/1987 | Smith et al. |
| 4,725,657 A | 2/1988 | Shibanai |
| 4,735,739 A | 4/1988 | Floyd et al. |
| 4,758,467 A | 7/1988 | Lempriere |
| 4,788,060 A | 11/1988 | Endicott et al. |
| 4,803,195 A | 2/1989 | Holzner |
| 4,806,572 A | 2/1989 | Kellett |
| 4,856,541 A | 8/1989 | Kellett et al. |
| 4,865,221 A | 9/1989 | Jackson et al. |
| 4,882,221 A | 11/1989 | Bogart et al. |
| 4,891,227 A | 1/1990 | Thaman et al. |
| 4,891,228 A | 1/1990 | Thaman et al. |
| 4,904,524 A | 2/1990 | Yoh |
| 4,946,617 A | 8/1990 | Sheridan et al. |
| 4,948,585 A | 8/1990 | Schlein |
| 5,017,365 A | 5/1991 | Niedbala |
| 5,063,062 A | 11/1991 | Greenspan et al. |
| 5,091,102 A | 2/1992 | Sheridan |
| 5,112,612 A | 5/1992 | Garvey et al. |
| 5,139,687 A | 8/1992 | Borgher, Sr. et al. |
| 5,185,155 A | 2/1993 | Behan et al. |
| 5,232,613 A | 8/1993 | Bacon et al. |
| 5,236,615 A | 8/1993 | Trinh et al. |
| 5,246,611 A | 9/1993 | Trinh |
| 5,250,728 A | 10/1993 | Parker et al. |
| 5,254,109 A | 10/1993 | Smith et al. |
| 5,284,972 A | 2/1994 | Parker et al. |
| 5,292,533 A | 3/1994 | McMahon et al. |
| 5,302,446 A | 4/1994 | Horn |
| 5,348,667 A | 9/1994 | Bacon et al. |
| 5,376,287 A | 12/1994 | Borcher, Sr. et al. |
| 5,449,822 A | 9/1995 | Parker et al. |
| 5,466,460 A | 11/1995 | McMahon et al. |
| 5,525,345 A | 6/1996 | Warner et al. |
| 5,538,732 A | 7/1996 | Smith et al. |
| 5,552,206 A | 9/1996 | Knoke et al. |
| 5,552,378 A | 9/1996 | Trinh et al. |
| 5,605,749 A | 2/1997 | Pike et al. |
| 5,620,694 A | 4/1997 | Girardot |
| 5,621,008 A | 4/1997 | Ptchelintsev |
| 5,648,083 A | 7/1997 | Blieszner et al. |
| 5,661,170 A | 8/1997 | Chodosh |
| 5,683,971 A | 11/1997 | Rose et al. |
| 5,698,475 A | 12/1997 | Vlasblom |
| 5,702,992 A | 12/1997 | Martin et al. |
| 5,750,122 A | 5/1998 | Evans et al. |
| 5,814,188 A | 9/1998 | Vinson et al. |
| 5,821,215 A | 10/1998 | Crudden et al. |
| 5,837,664 A | 11/1998 | Black |
| 5,866,110 A | 2/1999 | Moore et al. |
| 5,869,441 A | 2/1999 | Fair et al. |
| 5,871,762 A | 2/1999 | Venkitaraman et al. |
| 5,914,177 A | 6/1999 | Smith, III et al. |
| 5,951,991 A | 9/1999 | Wagner et al. |
| 5,971,841 A | 10/1999 | Tintelnot |
| 5,972,361 A | 10/1999 | Fowler et al. |
| 5,980,931 A | 11/1999 | Fowler et al. |
| 5,993,504 A | 11/1999 | Nonomura et al. |
| 6,054,450 A | 4/2000 | Shin et al. |
| 6,060,149 A | 5/2000 | Cabell et al. |
| 6,063,390 A | 5/2000 | Farrell et al. |
| 6,063,397 A | 5/2000 | Fowler et al. |
| 6,074,655 A | 6/2000 | Fowler et al. |
| 6,087,452 A | 7/2000 | Stewart et al. |
| 6,099,776 A | 8/2000 | Tintelnot |
| 6,103,644 A | 8/2000 | Sheridan |
| 6,132,746 A | 10/2000 | Hasenoehrl et al. |
| 6,132,841 A | 10/2000 | Guthrie et al. |
| 6,153,208 A | 11/2000 | McAtee et al. |
| 6,156,323 A | 12/2000 | Verdicchio et al. |
| 6,217,889 B1 | 4/2001 | Lorenzi et al. |
| 6,242,411 B1 | 6/2001 | D'Ambrogio et al. |
| 6,280,757 B1 * | 8/2001 | McAtee et al. ............ 424/402 |
| 6,391,835 B1 | 5/2002 | Gott et al. |
| 6,422,933 B1 | 7/2002 | Tintelnot |
| 6,491,937 B1 * | 12/2002 | Slavtcheff et al. .......... 424/402 |
| 6,495,151 B1 * | 12/2002 | McAtee et al. ............ 424/402 |
| 6,579,158 B1 | 6/2003 | Tintelnot |
| 6,616,641 B1 | 9/2003 | Sheridan |
| 6,638,527 B1 | 10/2003 | Gott et al. |
| 6,955,817 B1 * | 10/2005 | McAtee et al. ............ 424/402 |
| 2001/0041529 A1 | 11/2001 | Tintelnot |
| 2001/0046513 A1 | 11/2001 | Gott et al. |
| 2003/0022572 A1 | 1/2003 | Gott et al. |
| 2003/0100236 A1 | 5/2003 | Seth et al. |
| 2003/0113364 A1 | 6/2003 | McAtee et al. |
| 2003/0199838 A1 | 10/2003 | Sheridan |
| 2003/0228352 A1 | 12/2003 | Hasenoehrl et al. |

FOREIGN PATENT DOCUMENTS

| | | |
|---|---|---|
| CN | 1102211 A | 5/1995 |
| CN | 1106704 A | 8/1995 |
| CN | 1135320 A | 11/1996 |
| DE | 24 02 730 | 7/1975 |
| DE | 24 60 239 | 7/1975 |
| DE | 24 37 165 | 1/1976 |
| EP | 0186208 A | 7/1986 |
| EP | 0353013 A2 | 1/1990 |
| EP | 0485212 A1 | 5/1992 |
| EP | 0550067 B1 | 7/1993 |
| EP | 0613675 A1 | 9/1994 |
| EP | 0615720 A1 | 9/1994 |
| EP | 0 834 307 A2 | 4/1998 |
| EP | 0 976 392 A1 | 2/2000 |
| FR | 2271808 | 12/1975 |
| FR | 2538238 | 6/1984 |
| GB | 0 840 399 A | 7/1960 |
| GB | 1577926 A | 10/1980 |
| GB | 2163947 A | 3/1986 |
| GB | 2218430 A | 11/1989 |
| GB | 2297490 A | 8/1996 |
| JP | 55-75500 A | 6/1980 |
| JP | 58-112542 | 7/1983 |
| JP | 63-097699 | 4/1988 |
| JP | 01-246478 | 10/1989 |
| JP | 5-117699 A2 | 5/1993 |
| JP | 08-141012 | 6/1996 |
| JP | 09-151400 | 6/1997 |
| JP | 09-216809 | 8/1997 |
| WO | WO 89/03639 A1 | 5/1989 |
| WO | WO 93/05141 A1 | 3/1993 |
| WO | WO 93/21899 A1 | 11/1993 |
| WO | WO 94/02674 A1 | 2/1994 |
| WO | WO 94/27569 A1 | 12/1994 |
| WO | WO 95/00116 A2 | 1/1995 |
| WO | WO 95/16824 A1 | 6/1995 |
| WO | WO 96/14835 A1 | 10/1995 |
| WO | WO 95/31189 A1 | 11/1995 |
| WO | WO 96/04937 A1 | 2/1996 |

| | | |
|---|---|---|
| WO | WO 96/06595 A1 | 3/1996 |
| WO | WO 96/24329 A1 | 8/1996 |
| WO | WO 96/24723 A1 | 8/1996 |
| WO | WO 96/34035 A1 | 10/1996 |
| WO | WO 96/36315 A1 | 11/1996 |
| WO | WO 97/00001 A2 | 1/1997 |
| WO | WO 97/07781 A1 | 3/1997 |
| WO | WO 97/16066 A1 | 5/1997 |
| WO | WO 97/40126 A1 | 10/1997 |
| WO | WO 97/45256 A1 | 12/1997 |
| WO | WO 99/13861 A1 | 3/1999 |
| WO | WO 99/37476 A1 | 7/1999 |
| WO | WO 01/13880 A1 | 3/2001 |
| WO | WO 01/35923 A1 | 5/2001 |
| WO | WO 03/44153 A1 | 5/2003 |
| WO | WO 03/63807 A1 | 8/2003 |

OTHER PUBLICATIONS

Blue Apertured Cloth (see attached three letters to Unilever).

Tender Bath, Westgate Laboratories, Edison, NJ, 1987. (Product Description—product believed to have been test marketed in Sep. 1986).
Buf-Puf Singles Skin Conditioning, labeling, copyright 1991.
Buf-Puf Singles Oil-Free, labeling, copyright 1991.
Buf-Puf Singles With Cleanser for Normal to Dry Skin, labeling, copyright 1996.
Buf-Puf Singles With Cleanser for Normal to Oily Skin, labeling, copyright 1995.
Buf-Puf article photocopied actual size.
Test records.
DIN 53 902.
EN 12728.
Rompp Chemie Lexikon, 9. Auflage, Georg Thieme Verlag, Stuttgart, 1990, Stichwort: Harte des Wassers.
A. Domsch, Die kosmetischen Praparate, Band 2, 4. Auflage, Verlag fur chem . . . Industrie, H. Ziolkowsky KG, Augsburg, 1992, Kap. 3.1.

* cited by examiner

CLEANSING ARTICLES FOR SKIN OR HAIR

CROSS REFERENCE TO RELATED APPLICATION

This application claims the benefit of U.S. Provisional Application No. 60/387,305, filed Jun. 7, 2002.

TECHNICAL FIELD

The present invention relates to disposable personal cleansing articles useful for cleansing, and optionally conditioning, the skin or hair, and more particularly to a disposable, cleansing article comprising a nonwoven substrate and a lathering surfactant component wherein the substrate includes an elastomeric component. These cleansing articles are used by the consumer by wetting the article with water and by thereafter forming a lather by rubbing the article against itself and/or against skin or hair.

BACKGROUND OF THE INVENTION

Personal cleansing products have traditionally been marketed in a variety of forms such as bar soaps, creams, lotions, and gels. These cleansing formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use. Personal cleansing products are frequently used with, or marketed in the form of, articles that employ a substrate or other implement that carries a cleansing material or is used to deliver a cleansing material to the skin or hair.

Traditional forms of personal cleansing products and articles may be very useful for providing efficacious cleansing and lathering. Such conventional products and articles, however are less suitable for also simultaneously providing other desirable effects such as delivering a skin or hair conditioning benefit. One solution to this problem is to use separate cleansing and conditioning products or articles. However, this is not always convenient or practical, and many consumers would prefer to use a single article which can both cleanse and condition the skin or hair. In a typical cleansing composition or product, the conditioning ingredients are difficult to formulate because many conditioners are incompatible with the surfactants, resulting in an undesirable non-homogenous mixture. To obtain a homogeneous mixture with conditioning ingredients, and to prevent the loss of conditioning ingredients before deposition, additional ingredients, e.g. emulsifiers, thickeners, and gellants are often added to suspend the conditioning ingredients within a surfactant mixture. This results in an aesthetically pleasing homogenous mixture, but often results in poor deposition of conditioning ingredients onto skin or hair because the conditioners are emulsified and not efficiently released during cleansing. Also, many conditioning agents have the disadvantage of suppressing lather generation. Lather suppression is a problem because many consumers seek cleansing articles that provide a rich, creamy, and generous lather.

Therefore, it is seen that conventional cleansing products and articles which attempt to combine surfactants and other materials such as conditioning ingredients suffer from disadvantages inherently resulting from the incompatibilities of surfactants and conditioners. A need clearly exists to develop cleansing systems which provide effective cleansing, effective lathering and yet can also, if desired, consistently provide other benefits such as sufficient conditioning in a single article.

It is also highly desirable to deliver cleansing and preferably conditioning benefits from a disposable, single use article. Disposable articles are convenient because they obviate the need to carry cumbersome bottles, bars, jars, tubes, and other forms of both cleansing and conditioning articles. Disposable articles are also a more sanitary alternative to the use of a sponge, washcloth, or other cleansing implement intended for multiple reuse, because such implements develop bacterial growth, unpleasant odors, and other undesirable characteristics related to repeated use.

SUMMARY OF THE INVENTION

The present invention relates to disposable, single use personal cleansing articles especially useful for cleansing facial skin. Each such article comprises a) a water-insoluble, nonwoven substrate having an elastomeric component and at least one cleansing surface; and b) from about 0.5% to 250% by weight of the substrate of a lathering surfactant which is releasably associated with the substrate. Some of the cleansing articles described herein contain one or more water-soluble or water-insoluble conditioning agents in addition to the lathering surfactant component.

The present invention also relates to methods for manufacturing cleansing articles of the configuration described herein. Also, the present invention provides methods for cleansing, and optionally conditioning, the skin or hair using the articles described herein.

DETAILED DESCRIPTION OF THE INVENTION

The essential elements of cleansing articles of the present invention, i.e., the nonwoven substrate with an elastomeric component and the lathering surfactant, as well as a wide variety of optional elements, are described in detail as follows. All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

As used herein, the term "elastomeric component" refers to materials that extend in at least one direction when a force is applied and return to approximately their original dimensions after the force is released.

By a "lathering surfactant" is meant a surfactant, which when combined with water and mechanically agitated generates a foam or lather. Preferably, these surfactants should be mild, which means that these surfactants provide sufficient cleansing or detersive benefits but do not overly dry the skin or hair (e.g., removing too much natural oil and/or moisture), and yet meet the lathering criteria described above.

The term "lathering product" or "lathering article," as used herein, means that the product or article contains enough of the surfactants described herein that it can generate at least 30 ml of Lather Volume, as described herein in the Lather Volume Test. These Lather Volume measurements are conducted with a medium hardness water (8–10 grains per gallon) at 35° C. (95° F.).

The terms "disposable" or "single use", are used herein in their ordinary sense to mean an article that is disposed or discarded after a typical usage event.

The term "conditioning component," as used herein, means a combination of the conditioning agents.

The term "water-activated," as used herein, means that the present invention is presented to the consumer in a form to be used after it is wetted with water. It is found that these articles produce a lather or are "activated" by contacting them with water and then further subjecting the article to mechanical forces, such as rubbing.

The term "substantially dry," as used herein, means that prior to use the article is substantially free of water and generally feels dry to the touch. Thus, the articles of the present invention will generally comprise less than about 20% by weight of water, preferably less than about 10% by weight of water, and more preferably less than about 5% by weight of water, the forgoing measured in a dry environment, e.g., low humidity. One of ordinary skill in the art would recognize that the water content of a article such as in the present invention can vary with the relative humidity of the environment.

The term "mild" as used herein in reference to the lathering surfactants and articles of the present invention means that the articles of the present invention demonstrate skin mildness comparable to a mild alkyl glyceryl ether sulfonate (AGS) surfactant based synthetic bar, i.e., synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H—H_2O$) which passes from the test solution through the skin epidermis into the physiological buffer contained in the diffusate chamber. This test is described by T. J. Franz in the J. Invest. Dermatol., 1975, 64, pp. 190–195; and in U.S. Pat. No. 4,673,525, to Small et al., issued Jun. 16, 1987. Other testing methodologies for determining surfactant mildness well known to one skilled in the art can also be used.

The personal cleansing articles of the present invention comprise the following essential components: (A) a water-insoluble, nonwoven substrate having an elastomeric component and at least one cleansing surface, and (B) at least one lathering surfactant added onto or impregnated into the substrate. The articles of the present invention can further optionally comprise a conditioning component added onto or impregnated into the substrate.

Water Insoluble Nonwoven Substrate

The products of the present invention comprise a water insoluble, nonwoven substrate having at least one cleansing surface. By "water insoluble" is meant that the substrate does not dissolve in or readily break apart upon immersion in water. The water insoluble substrate is the implement or vehicle for delivering the lathering surfactant and optionally the conditioning component of the present invention to the skin or hair to be cleansed and conditioned. Without being limited by theory, it is believed that the substrate, by providing mechanical forces and agitation provides a lather generating effect and also aids in the deposition of the conditioning component.

A wide variety of materials can be used as the substrate. The following nonlimiting characteristics are desirable: (i) sufficient wet strength for use, (ii) sufficient abrasivity, (iii) sufficient loft and porosity, (iv) sufficient thickness, and (v) appropriate size.

The term "nonwoven" refers to fabrics made of fibers held together by interlocking or inter-fiber bonding which are not woven, knitted, felted, or the like. However, the nonwoven substrate referred to herein may comprise fibers that are initially substantially unbonded which are subsequently bonded to each other. A nonwoven layer is comprised of fibers which are not woven into a fabric but rather are formed into a sheet, mat, or pad layer. The fibers can either be random (i.e., randomly aligned) or they can be carded (i.e., combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," Nonwoven World (1987); The Encyclopedia Americana, vol. 11, pp. 147–153, and vol. 26, pp. 566–581 (1984); U.S. Pat. No. 4,891,227, to Thaman et al., issued Jan. 2, 1990; and U.S. Pat. No. 4,891,228.

The substrate can have a basis weight of between 15 to about 96 grams per square meter. In accordance with a particular embodiment, the basis weight of the substrate is between about 36 to about 84 grams per square meter, and in a more particular embodiment, the basis weight of the substrate is about 42 to about 78 grams per square meter.

Substrates made from natural materials consist of webs or sheets most commonly formed on a fine wire screen from a liquid suspension of the fibers. See C. A. Hampel et al., The Encyclopedia of Chemistry, third edition, 1973, pp. 793–795 (1973); The Encyclopedia Americana, vol. 21, pp. 376–383 (1984); and G. A. Smook, Handbook of Pulp and Paper Technologies, Technical Association for the Pulp and Paper Industry (1986).

Methods of making nonwoven substrates are well known in the art. Generally, these nonwoven substrates can be made by air-laying, water-laying, meltblowing, coforming, spin-bonding, or carding processes in which the fibers or filaments are first cut to desired lengths from long strands, passed into a water or air stream, and then deposited onto a screen or belt through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates used in the present invention can consist of a single layer or multiple layers. In addition, a multilayered substrate can include films and other nonfibrous materials.

In accordance with the present invention, at least a portion of the substrate comprises an elastomeric component. By combining a nonwoven web with an elastomeric component as described herein, a substrate can be provided which exhibits out-of-plane (Z-direction) deformation of the substrate which gives added texture to the surface of the cleansing article. The added texture because of the contour or waviness of the substrate can aid in the incorporation of air during the lathering process, thereby improving lather generation.

The elastomeric component of the nonwoven substrate can, for example, be a backing material or an elastomeric filament. The elastomeric component and nonwoven material can be combined in various ways to form the substrate of the invention. The elastomeric component can be an integral part of the nonwoven web, such as a reinforcement warp yarn. Alternatively, the nonwoven web can be a separate web or layer applied to one or both sides of an elastomeric backing material.

Figure 1:
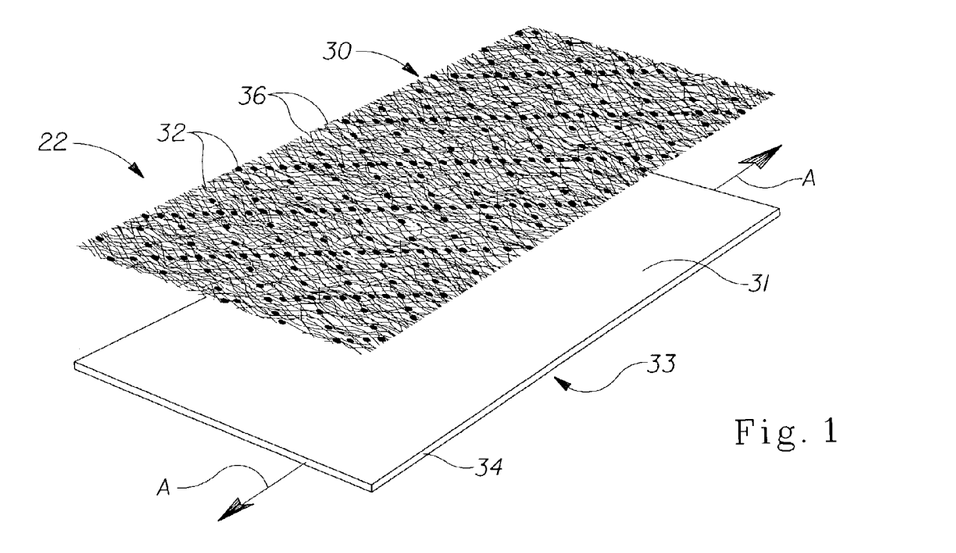
FIG. 1 is a perspective view of the filaments and the backing used to form a cleansing article in accordance with one embodiment of the present invention prior to the filaments being positioned or laid down on the backing.
Figure 2:
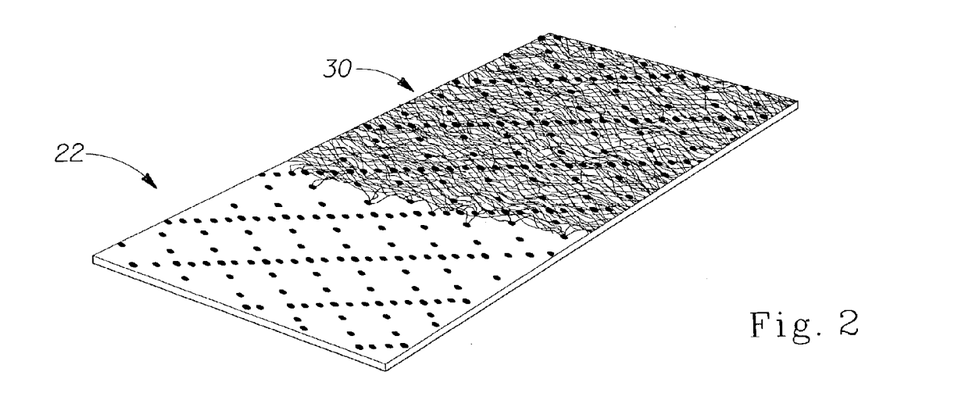
FIG. 2 is a perspective view of the cleansing cloth of FIG. 1 when the backing is in its elongated orientation.
Figure 3:
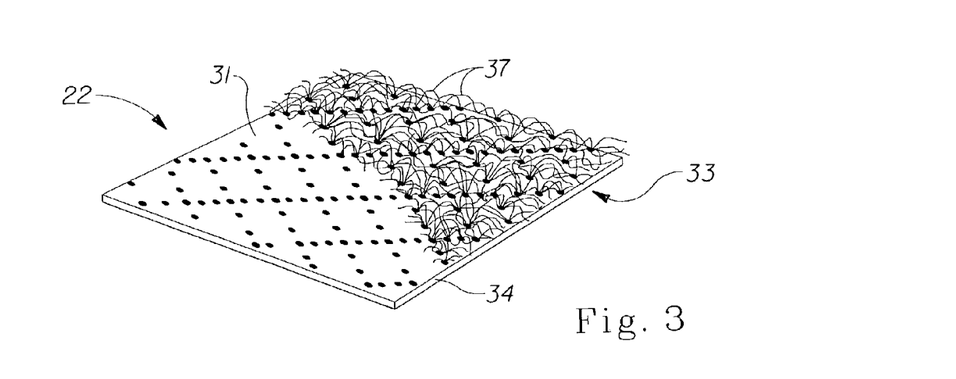
FIG. 3 is a perspective view of the cleansing cloth of FIG. 1 when the backing is in its relaxed orientation.

FIGS. 1–3 show a nonwoven substrate in accordance with one embodiment of the present invention, wherein the elastomeric component comprises a backing material. FIG. 1 shows the backing 34 and the nonwoven web 30 used to form the substrate 22 prior to their association. The elastomeric backing material 34 is shown in its elongated orientation (stretched in a direction parallel to the line designated A—A). The nonwoven web 30 preferably comprises a multiplicity of filaments 36 having unsecured regions and fixed regions. The fixed regions comprise inter-fiber bonds 32. As used herein, the term "inter-fiber bonds" refers to bonds that join one or more filaments to one or more other filaments. The term "joined" encompasses configurations whereby an element is directly secured to another element and configurations whereby an element is indirectly secured to another element by affixing an element to intermediate member(s) which in turn are affixed to another element.

FIG. 2 shows a preferred embodiment of the substrate 22 where the backing 34 is in its elongated orientation after the nonwoven web 30 has been positioned on and joined to the first surface 31 of the backing 34. The filaments 36 of the nonwoven web 30 are preferably in an untensioned state when they are joined to the elongated backing 34. This helps to ensure that the unsecured regions 35 of the filaments 36 will become "shirred" when the backing 34 contracts to its relaxed orientation (shown in FIG. 3). The term "shirred" as used herein, refers to the gathering of the filaments 36 of the nonwoven web 30 caused by the contraction of the backing 34 from its elongated orientation to its relaxed orientation such that portions of the filaments 36 that are not secured to the backing 34 or other filaments 36 bend away from the first surface 31 of the backing 34. The shirred unsecured regions 35 of the filaments 36 form regions 37 capable of holding more lathering surfactant and providing texture.

As described in further detail below, the nonwoven web 30 is joined to the backing 34 with construction bonds. The construction bonds form a particular construction bond pattern that improves the effectiveness of the nonwoven web 30 as a substrate for a cleansing article. (The term "construction bond" as used herein, refers to bonds that join portions of the nonwoven web 30 to the backing 34.)

A nonwoven web in accordance with this embodiment of the present invention is described in more detail in U.S. Pat. No. 5,595,567, to King et al. The regions 37 of the nonwoven substrate of this embodiment are preferably formed from filaments 36 comprised in a nonwoven web positioned on and secured to the backing 34. As used herein, the term "filament" defines a member having a high ratio of length to diameter or width. Thus, a filament may be a fiber, a thread, a strand, a yarn or any other member or combination of these members, including filaments that are preattached together in nonwoven webs, as are known in the art. Suitable materials for such filaments 36 include natural fibers such as cotton or wool; synthetic fibers of nylon, polyamides, polyesters, or polyolefins; spun yarns; polyethylene fibers; polypropylene fibers; nylon fibers, nonwoven webs; or any other material or combination of materials known in the art and suitable for use herein.

The filaments 36 may be manufactured using a number of manufacturing techniques including those such that the filaments are spun, blown, or the like. Preferably, each filament 36 comprises polypropylene fibers of between about 2 and about 15 denier. The individual filaments 36 are preferably comprised in a nonwoven web 30 which, prior to being combined with backing 34, has a basis weight of between about 12 g/m$^2$ to about 48 g/m$^2$, more preferably between about 18 g/m$^2$ and about 30 g/m$^2$. The nonwoven web 30 may comprise filaments 36 having similar or different deniers and lengths. Further, the nonwoven web 30 may comprise a mixture of filaments 36 comprising different materials. Some nonwoven webs comprising suitable filaments include the carded polypropylene nonwoven web manufactured by the Veratec Nonwoven Group of the International Paper Company, of Walpole, Mass. under the trade name P-11, the spunbonded polypropylene nonwoven web P-9, and the carded polypropylene nonwoven web P-8. Other suitable nonwoven webs comprising suitable filaments include COROVON spunbonded polypropylene manufactured by Corovin GmbH of Germany, and CELESTRA manufactured by the James River Corporation.

The nonwoven web 30 is preferably positioned on and joined with the backing 34 while the backing 34 is in an elongated orientation and while the filaments 36 are in an untensioned condition. While the filaments 36 could conceivably be positioned on the backing 34 in a tensioned or unstable state, such is not preferred to provide maximum shirring of the filaments 36. The filaments 36 may be positioned or laid down on the backing 34 by any method or means that is known in the art.

The backing 34 of this aspect of the present invention is that part of substrate 22 to which the nonwoven web 30 is secured. The backing 34 is preferably comprised of an elastomeric material. Elastomeric materials have an elongated orientation (when force is applied), a relaxed orientation (when force is removed), and a path of response along which the backing 34 contracts from its elongated orientation to its relaxed orientation. In a preferred embodiment of the present invention, the backing 34 will be elongated in the machine direction prior to its association with the nonwoven web 30. (As used herein, the term "machine direction" refers to the direction in which the materials move as the materials move forward through any processing steps. The term "cross machine direction" refers to the direction perpendicular to the machine direction.)

The backing 34 of the present invention may take on a number of different configurations. For example, the backing 34 may comprise a thin film having a uniform or varying thickness, slits, holes, deformations or the like; a laminate of two or more films; single or multiple strands of fibers, films or laminates; or any combination of the above. In one preferred embodiment, the backing 34 comprises a thin film of about 0.013 mm. to about 1.0 mm. (about 0.0005 in. to about 0.04 in.). In a particularly preferred embodiment, the elastomeric film has a thickness of between about 0.013 mm. to about 0.38 mm (about 0.0005 in. to about 0.015 in.).

The backing 34 may comprise any of a number of different elastomeric materials known in the art. The backing 34 preferably has an elastic modulus between about 1 and about 30 PSI and more preferably between about 5 and about 15 PSI. (The elastic modulus calculation is preferably determined on the strain interval of about 5% to about 50% elongation of any convenient gage length using the original cross sectional area of the sample prior to straining the sample to determine the elastic modulus.) Further, the backing 34 should be capable of elongation from about 10 to about 500 percent in at least one direction without rupture. More preferably, the backing 34 should be capable of between about 10 percent and about 500 percent elongation without rupture, not exhibit excessive necking or thinning when elongated, or exhibit excessive hysteresis or delamination upon elongation. Examples of suitable backing materials include but are not limited to butadiene/acrylonitrile copolymers, styrene-butadiene-styrene block copolymers, polyurethane elastomers, natural rubber, ethylene propylene-dimonomers, polypropylene films, as well as polyethylene films available from the Clopay Corporation of Cincinnati, Ohio (e.g. Clopay 1401), and Tredegar Film Products, Inc of Terre Haute, Ind., and the styrene-isoprene-styrene block copolymer film EXX500 available from the Exxon Chemical Company of Lake Zurich, Ill.

A construction bond is that part of the substrate 22 which joins the nonwoven web 30 with the backing 34. The construction bonds may comprise any number of different types of bonds as are known in the art. For example, the construction bonds may comprise adhesives, including pressure sensitive adhesives, hot melt adhesives that are extruded, slot coated, screen or gravure printed; ultrasonic bonds; heat bonds, pressure bonds, friction bonds, autogenous bonds or any combination of these or any other bonding methods as are known in the art. Some examples of preferred construction bond adhesives comprise hot melt adhesives manufactured by the Findley Adhesives Corporation of Wauwatosa, Wis. under the trade names H2031, H2085, and H2305.

In accordance with another embodiment of the present invention, the substrate comprises a non-woven, composite material, which is capable of holding a sufficient amount of lathering surfactant. A suitable composite material for use in accordance with this aspect of the invention is described in U.S. Pat. No. 5,552,206, to Knoke et al. The composite contains a nonwoven material having a mass per unit area of 10 to 40 g/m$^2$ with elastic warp reinforcement, which warp reinforcement contains 5 to 25 g/m$^2$ textured warp yarn having a primary elongation of 10 to 35% with a total denier of 30 to 120 dtex. The weight ratio of warp yarn:nonwoven fabric is from 1:3 to 3:1. The thread count is 1.8 to 9.84/cm (3 to 25/inch). The composite material is manufactured in a warp knitting machine having a nonwoven fabric feed, the nonwoven fabric being reinforced with textured filaments and, at the end, the composite being thermofixed. After the warp yarn is fed and prior to the thermofixing, the composite fabric is subjected to a complete tensionless shrinking process. The composite fabric exhibits a final elongation in the longitudinal direction of 50 to 120%.

The nonwoven material used as the substrate in accordance with this aspect of the invention is characterized by an excellent surface texture or contour, making it particularly useful as a substrate for a cleansing article. Warp yarns made of nylon 6 or nylon 66 proves to be particularly suitable for this substrate, because these produce an especially flexible elasticity. Side-by-side bicomponent filaments, with nylon 6 or nylon 66 components on one hand, and polyester components on the other provide substrates having particularly good final appearance. Warp yarns made of polyester can be used to produce particularly color-stable substrates.

It is expedient to select soft nonwoven fabrics as the base. Spot-heat-sealed, fiber-bonded, nonwoven fabrics are preferred. A special softness is attained when the nonwoven fabric is bonded using water jets. Moreover, for obtaining an especially high internal strength, thermoplastic binding fibers can be included as well.

The substrates used to form the personal cleansing articles of the present invention may contain apertures or openings in the cleansing surface of the substrate. Such apertures may be generally circular in shape or may be openings of other shapes, including squares, rectangles, trapezoids, diamonds, hexagons, irregular shapes and the like. Such apertures need not be uniform in size and shape, but preferably will be substantially uniform in both size and shape.

The substrate can be made into a wide variety of shapes and forms including flat pads, thick pads, thin sheets, ball-shaped implements, irregularly shaped implements, and having sizes ranging from providing a cleansing surface area of at least about 5 cm$^2$. The exact size will depend upon the desired use and product characteristics. Especially convenient are square, circular, rectangular, or oval pads having a cleansing surface area of from about 6 cm$^2$ to 1000 cm$^2$, preferably from about 65 cm$^2$ to about 775 cm$^2$, and more preferably from about 150 cm$^2$ to about 400 cm$^2$ and a thickness of from about 1 mil to about 500 mil, preferably from about 5 mil to about 250 mil, and more preferably from about 10 mil to about 100 mil.

Furthermore, it is desirable for the substrates of the present invention to have rounded corners. This feature prevents the tendency of water to accumulate at the corners of an unrounded rectangular, e.g., square, substrate. Corners, preferably all of the corners on the substrate, can be rounded to provide a radius of from about 1 to 4 cm. Preferably the rounded corners will have a radius of from about 2 to 3 cm.

Lathering Surfactant

Besides the water-insoluble substrate, the articles of the present invention also comprise one or more lathering surfactants which are releasably associated with the water-insoluble substrate. Thus the lathering surfactants can be added onto or impregnated into the substrate. Generally this will be done prior to the point of use of the article, i.e., the surfactants will be combined with the article and the article dried before the article is ultimately wetted for use. Preferred articles of the present invention comprise a sufficient amount of one or more lathering surfactants such that the articles are capable of generating at least 30 ml of Lather Volume (medium hardness water at 35° C. (95° F.) according to the Lather Volume Test described below.

Generally the articles will contain from about 0.5% to 250%, by weight of the substrate, of a lathering surfactant that is releasably associated with the substrate. Preferably, the articles of the present invention comprise from about 0.5% to about 50%, more preferably from about 0.75% to about 30%, and most preferably from about 1% to about 20%, based on the weight of the water insoluble substrate, of a lathering surfactant component.

By a lathering surfactant is meant a surfactant, which when combined with water and mechanically agitated generates a foam or lather sufficient to cause the article, as a whole, to provide a lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lather surfactants, amphoteric lathering surfactants, and mixtures thereof. Nonlimiting examples of lathering surfactants useful in the compositions of the present invention are disclosed in U.S. Pat. No. 6,280,757, to McAtee et al., issued Aug. 28, 2001. Generally, the lathering surfactants do not strongly interfere with deposition of any conditioning agents that are present, e.g., are fairly water soluble, and usually have an HLB value of above 10. Cationic surfactants can also be used as optional components, provided they do not negatively impact the overall lathering characteristics of the required lathering surfactants.

Anionic Lathering Surfactants

Nonlimiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Nonlimiting examples of preferred nonionic surfactants for use herein are those selected form the group consisting of $C_8$–$C_{14}$ glucose amides, $C_8$–$C_{14}$ alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amnphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Nonlimiting examples of amphoteric or zwitterionic surfactants are those selected from the group consisting of betaines, sultaines, hydroxysultaines, alkyliminoacetates, imninodialkanoates, aminoalkanoates, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the nonionic lathering surfactant is selected from the group consisting of lauramine oxide, cocoamine oxide, decyl polyglucose, lauryl polyglucose, sucrose cocoate, $C_{12\text{-}14}$ glucosamides, sucrose laurate, and mixtures thereof, and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Lather Volume Test

The articles of the present invention preferably comprise enough of the lathering surfactant such that the articles are capable of generating greater than or equal to about 30 ml, more preferably greater than or equal to about 50 ml, even more preferably greater than or equal to about 75 ml, and most preferably greater than or equal to about 150 ml of Average Lather Volume. The Average Lather Volume is a measurement determined by the Lather Volume Test. This test provides a consistent measurement of the volume of lather/foam generated by the articles described herein. The Lather Volume Test protocol is described as follows:

(1) Hands are washed with Ivory bar before conducting the test. This step removes any soils which may affect the accuracy of the measurement.

(2) The test article is held open in the non-dominant hand with the edges turned up.

(3) 10 ml. of water (medium hardness of about 8-10 grains per gallon) at 35° C. (95° F.) is added onto the test article via a 10 cc syringe or a Brinkmann repipetter.

(4) The lather is then generated by rubbing the test article with the dominant hand in a circular motion between the palms for 6 seconds (~2 rotations per second), using moderate pressure (e.g., 4 oz.), and allowing the article to ball-up between the palms of the hand.

(5) The test article is then held open in the non-dominant hand and an additional 10 ml of water (medium hardness of about 8-10 grains per gallon) at 35° C. (95° F.) is added onto the test article via a 10 cc syringe or a Brinkmann repipetter. The wetted article is again rubbed with the dominant hand (3 rotations) using moderate force (e.g, 4 oz.) so that the test article becomes balled-up between the palms.

(6) The test article is then opened and rubbed 5 times by holding one edge of the article in one hand and rotating the hand holding the other side to further activate lather.

(7) The test article is then flipped over and Step #6 is repeated using the other hand.

(8) The lather is gathered by holding the test article in a cupped hand and scraping the lather off the test article with the other hand, being careful to only scrape lather from the test article. The lather from the test article is placed into a graduated cylinder or beaker big enough to hold the generated lather. This procedure is repeated 5 times on the same test article, and the lather from each iteration is accumulated in the same graduated cylinder or beaker. The total accumulated lather from these iterations is designated as the Lather Volume.

(9) To achieve consistent results, the Average Lather Volume is reported as the average of three test sample replications of Steps 1–8.

Conditioning Component

The articles of the present invention will preferably further comprise a conditioning component which is useful for providing a conditioning benefit to the skin or hair during the use of the article. The conditioning component can comprise from about 0.05% to about 99%, preferably from about 0.1% to about 50%, and more preferably from about 1% to about 25% by weight of said water insoluble substrate.

The conditioning component useful in the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e., less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e.,greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process.

Nonlimiting examples of conditioning agents useful as conditioning agents include those selected from the group consisting of fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.

More particularly, the conditioning agent may be selected from the group consisting of paraffin, mineral oil, petrolatum, stearyl alcohol, cetyl alchohol, cetearyl alcohol, behenyl alcohol, C10–30 polyesters of sucrose, stearic acid, palmitic acid, behenic acid, oleic acid, linoleic acid, myristic acid, lauric acid, ricinoleic acid, steareth-1–100, cetereath 1–100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, and silicone waxes.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415–417 (1993).

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36–37, 76, 78–80, 82

(1961); and International Cosmetic Ingredient Dictionary, Fifth Edition, vol. 1, p. 537 (1993).

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991.

The conditioning component preferably used in the present invention may also comprise a conditioning emulsion which is useful for providing a conditioning benefit to the skin or hair during the use of the article. The term "conditioning emulsion" as used herein means the combination of an internal phase comprising a water soluble conditioning agent that is enveloped by an external phase comprising an oil soluble agent. In preferred embodiments, the conditioning emulsion would further comprise an emulsifier. The conditioning emulsion comprises from about 0.25% to about 150%, preferably from about 0.5% to about 100%, and more preferably from about 1% to about 50% by weight of said water insoluble substrate. By a conditioning emulsion is meant a combination of an internal phase comprising a water soluble conditioning agent that is enveloped by an external phase comprising an oil soluble agent. In preferred embodiments, the conditioning emulsion would further comprise an-emulsifier.

The conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

Preferred embodiments of the present invention which contain conditioning emulsions comprise an emulsifier capable of forming an emulsion of the internal and external phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from about 0.1% to about 20%, preferably from about 1% to about 10%, and more preferably from about 3% to about 6% by weight of the conditioning emulsion.

The emulsifiers useful in the present invention typically are oil soluble or miscible with the oil soluble external phase materials, especially at the temperature at which the lipid material melts. It also should have a relatively low HLB value. Emulsifiers suitable for use in the present invention have HLB values typically in the range of from about 1 to about 7 and can include mixtures of different emulsifiers. Preferably, these emulsifiers will have HLB values from about 1.5 to about 6, and more preferably from about 2 to about 5.

Weight Ratios and Weight Percentages

In the present invention, the weight ratio of the lathering surfactant to the conditioning component is preferably less than about 40:7, more preferably less than about 5:1, even more preferably less than about 2.5:1, and most preferably less than about 1:1.

In certain preferred embodiments of the present invention, the cleansing and conditioning component, which is defined as comprising a lathering surfactant and a conditioning component further comprising an oil soluble conditioning agent and a water soluble conditioning agent, the lathering surfactant comprises from about 1% to about 75%, preferably from about 10% to about 65%, and more preferably from about 15% to about 45%, by weight of the cleansing and conditioning component, and the conditioning component comprises from about 15% to about 99%, preferably from about 20% to about 75%, and more preferably from about 25% to about 55%, by weight of the cleansing and conditioning component.

Additional Ingredients

The compositions which are added onto or impregnated into the articles of the present invention may comprise a wide range of optional ingredients. Particularly useful are added polymers, various active ingredients, and cationic surfactants useful for delivering various non-conditioning or non-cleansing benefits of the skin or hair during the cleansing and conditioning process. Additional ingredients of these types are described in greater detail in Procter & Gamble; PCT Application No. WO 99/13861; published Mar. 25, 1999 (P&G Case 6840).

Other Optional Ingredients

The articles of the present invention can comprise a wide range of other optional components. These additional components should be pharmaceutically acceptable. The CTFA Cosmetic Ingredient Handbook, Second Edition, 1992, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

Methods of Manufacture

The disposable, single use personal care cleansing articles of the present invention can be manufactured by separately or simultaneously adding onto or impregnating into a water-insoluble substrate a lathering surfactant and optionally a conditioning component. If necessary, the resulting article can then be dried. By "separately" is meant that the surfactants and conditioning agents can be added sequentially, in any order without first being combined together. By "simultaneously" is meant that the surfactants and conditioning agents can be added at the same time, with or without first being combined together.

The lathering surfactant and/or the conditioning component can be added onto or impregnated into the substrate using any means known to those skilled in the art. These components can be applied using various spraying, soaking, coating or dipping techniques. Excess surfactant and/or conditioning component should be removed (e.g., by a nipping process). Thereafter, the treated substrate should be dried by conventional means.

When water or moisture is used or present in the manufacturing process, the resulting treated substrate is then preferably dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

Preferably, upon wetting with water during use, the articles of the present invention are capable of generating an Average Lather Volume of greater than or equal to about 30 ml, more preferably greater than or equal to about 50 ml, even more preferably greater than or equal to about 75 ml, and most preferably greater than or equal to about 150 ml.

Methods of Cleansing and Conditioning the Skin or Hair

The present invention also relates to a method of cleansing and conditioning the skin or hair with a personal cleansing article of the present invention. These methods comprise the steps of wetting with water a substantially dry, disposable, single use personal cleansing article comprising a water insoluble substrate, a lathering surfactant, and optionally a conditioning component, and contacting the skin or hair with such wetted article. In further embodiments, the present invention is also useful for delivering various active ingredients to the skin or hair.

The articles of the present invention are intended to be wetted with water prior to use. The article is wetted by immersion in water or by placing it under a stream of water.

Lather is generated from the article by mechanically agitating and/or deforming the article either prior to or during contact of the article with the skin or hair. Preferably, upon wetting, the articles of the present invention generate an Average Lather Volume of greater than or equal to about 30 ml, more preferably greater than or equal to about 50 ml, even more preferably greater than or equal to about 75 ml, and most preferably greater than or equal to about 150 ml. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

Without being limited by theory it is believed that the substrate significantly contributes to generation of lather and deposition of conditioning agents and any other active ingredients. It is believed that this increase in lathering and deposition is the result of the surface action of the substrate. As a result, milder and significantly lower amounts of surfactants may be employed. The decreased amount of required surfactant is believed to relate to the decrease in the drying effect of the skin or hair by the surfactants. Furthermore, the diminished amount of surfactant dramatically lowers the inhibitory action (e.g., via emulsification or direct removal by the surfactants) which surfactants exhibit regarding deposition of conditioning agents.

Further without being limited by theory, it is believed that the substrate also enhances deposition of conditioning agents and active ingredients. Since the invention is in dry form, the invention does not require emulsifiers, which can inhibit deposition of conditioning agents and active ingredients. Furthermore, because the skin conditioners and active ingredients are dried onto or impregnated into the substrate, they are transferred directly to the skin or hair by surface contact of the wetted article to the skin.

The substrate also enhances cleansing. The substrate can have differing textures on each side, e.g. a rough side and a smooth side. The substrate, especially a multilayered construction, acts as an efficient lathering and exfoliating implement. By physically coming into contact with the skin or hair, the substrate significantly aids in cleansing and removal of dirt, makeup, dead skin, and other debris.

Finally, a substrate as described herein provides the desired qualities (e.g., proper texture, thickness, and bulk) of a washcloth.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable, single use personal cleansing article especially useful for cleansing skin or hair, which article comprises:
   (A) a water-insoluble substrate having at least one cleansing surface; and
   (B) from about 0.5% to about 250% by weight of said substrate of a lathering surfactant releasably associated with said substrate;
   wherein said water-insoluble substrate comprises:
       an elastomeric backing having an elongated orientation, a relaxed orientation, and path of response along which said backing contracts from said elongated orientation to said relaxed orientation;
       a nonwoven web in contact with said backing said nonwoven web comprising filaments having unsecured regions and fixed regions, said fixed regions comprised inter-fiber bonds joining said filament; and
       at least one construction bond for joining said nonwoven web with said backing, wherein said unsecured regions of said filaments are shirred when said backing is caused to return to its relaxed orientation.

2. An article according to claim 1 wherein said lathering surfactant comprises from about 0.5% to about 50% by weight of said water insoluble substrate.

3. An article according to claim 2 which is substantially dry prior to use.

4. An article according to claim 1 wherein said backing comprises an elastomeric film selected from the group consisting of polyethylene film, polypropylene film, styrene-isoprene-styrene block copolymer film and styrene-butadiene-styrene block copolymer film.

5. An article according to claim 1 wherein said nonwoven web has a weight of 10–40 g/m$^2$ and said elastomeric backing comprises elastomeric warp yarn, wherein the weight ratio of warp yarn to nonwoven web is from 1:3 to 3:1 and wherein said water-insoluble substrate is characterized by an elongation of 50–120% in the longitudinal direction.

6. An article according to claim 5 wherein the warp yarn comprises at least one material selected from the group consisting of nylon 6, nylon 66 and polyester.

7. An article according to claim 1 further comprising a conditioning component added onto or impregnated into said substrate.

8. An article according to claim 7 wherein said conditioning component comprises at least one material selected from the group consisting of fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.

9. An article according to claim 8 wherein said conditioning component comprises at least one material selected from the group consisting of paraffin, mineral oil, petrolatum, stearyl alcohol, cetyl alcohol, cetearyl alcohol, behenyl alcohol, C10–30 polyesters of sucrose, stearic acid, palmitic acid, behenic acid, oleic acid, linoleic acid, myristic acid, lauric acid, ricinoleic acid, steareth-1-100, cetereath 1-100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, and silicone waxes.

10. An article according to claim 1 wherein said lathering surfactant is selected from the group consisting of anionic lathering surfactants, nonionic lathering surfactants, amphoteric lathering surfactants, and mixtures thereof.

11. An article according to claim 10 wherein said anionic lathering surfactant is selected from the group consisting of sarcosinates, sulfates, isethionates, phosphates, taurates, lactylates, glutamates and mixtures thereof; wherein said nonionic lathering surfactant is selected from the group consisting of amine oxides, alkyl glucosides, alkyl polyglucosides, polyhydroxy fatty acid amides, alkoxylated fatty acid esters, sucrose esters, and mixtures thereof; and wherein said amphoteric lathering surfactant is selected from the group consisting of betaines, sultaines, hydroxysultaines, alkyliminoacetates, iminodialkanoates, aminoalkanoates, and mixtures thereof.

12. An article according to claim 1 wherein the article is capable of generating an Average Lather Volume of greater than or equal to about 30 ml upon wetting.

13. An article according to claim 12 wherein the article is capable of generating an Average Lather Volume of greater than or equal to about 75 ml upon wetting.

14. An article according to claim 1, wherein said substrate has rounded corners, said corner having a radius of from about 2 to 3 cm.

* * * * *